(12) United States Patent
Idzko et al.

(10) Patent No.: US 9,333,216 B2
(45) Date of Patent: May 10, 2016

(54) URIDINE AND URIDINE ANALOGUES FOR TREATMENT OF SPECIFIC LUNG DISEASES, NAMELY COPD AND PULMONARY FIBROSIS

(75) Inventors: Marco Idzko, Freiburg (DE); Stephan Sorichter, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 68 days.

(21) Appl. No.: 14/238,584

(22) PCT Filed: Jul. 24, 2012

(86) PCT No.: PCT/EP2012/064481
§ 371 (c)(1),
(2), (4) Date: May 7, 2014

(87) PCT Pub. No.: WO2013/023882
PCT Pub. Date: Feb. 21, 2013

(65) Prior Publication Data
US 2014/0323427 A1    Oct. 30, 2014

(30) Foreign Application Priority Data

Aug. 12, 2011 (EP) .................... 11177357

(51) Int. Cl.
| | | |
|---|---|---|
| *A01N 43/04* | (2006.01) | |
| *A61K 31/70* | (2006.01) | |
| *A61K 31/7072* | (2006.01) | |
| *A61K 31/706* | (2006.01) | |
| *A61K 31/7064* | (2006.01) | |
| *A61K 31/7042* | (2006.01) | |
| *A61K 31/7052* | (2006.01) | |
| *A61K 9/00* | (2006.01) | |
| *A61K 45/06* | (2006.01) | |
| *A61K 31/7068* | (2006.01) | |

(52) U.S. Cl.
CPC ............. *A61K 31/7072* (2013.01); *A61K 9/008* (2013.01); *A61K 9/0019* (2013.01); *A61K 31/706* (2013.01); *A61K 31/7042* (2013.01); *A61K 31/7052* (2013.01); *A61K 31/7064* (2013.01); *A61K 31/7068* (2013.01); *A61K 45/06* (2013.01)

(58) Field of Classification Search
None
See application file for complete search history.

(56) References Cited

U.S. PATENT DOCUMENTS 7,638,501 B1 * 12/2009 Naviaux .................... 514/50

FOREIGN PATENT DOCUMENTS

| EP | 1 338 282 A1 | 8/2003 |
|---|---|---|
| WO | WO 89/03837 A1 | 5/1989 |
| WO | WO 99/09998 A1 | 3/1999 |
| WO | WO 2006/090235 A1 | 8/2006 |
| WO | WO 2007/002945 A2 | 1/2007 |

OTHER PUBLICATIONS

Weinberg et al. PLoS ONE (Feb. 2011), vol. 6, Issue 2, pp. 1-8.*
Evaldsson C et al., *Clinical and Experimental Immunology* (Feb. 2009) vol. 155(2), pp. 330-338.
Evaldsson C et al., *International Immunopharmacology* (Jun. 11, 2007) vol. 7, pp. 1025-1032.
Müller T et al., *Clinical and Experimental Allergy* (Oct. 1, 2010) vol. 40(10), pp. 1552-1560.
Namba T et al., *Cell Death and Differentiation* (Dec. 1, 2010) vol. 17, pp. 1882-1895.
Trevethick M.A., *Clinical and Experimental Allergy* (Oct. 2010) vol. 40(10), pp. 1436-1438.
Uppugunduri S et al., *International Immunopharmacology* (Sep. 2009) vol. 4, pp. 1241-1248.
Weinberg M., *PLoS ONE* (Jan. 1, 2011) vol. 6(2), E14709, pp. 1-8.

* cited by examiner

*Primary Examiner* — Patrick Lewis
(74) *Attorney, Agent, or Firm* — Chalin A. Smith; Smith Patent

(57) ABSTRACT

The present invention relates to the new indications of chronic obstructive pulmonary disease (COPD) and idiophathic lung fibrosis (IPF) for uridine and uridine analogues.

5 Claims, 3 Drawing Sheets

| Groups | | Results at 4 Months | | Results at 7 Months | |
|---|---|---|---|---|---|
| Exposure/Treatment 0-4 Months | Exposure/Treatment 4-7 Months | Lm (µm) | ISA (cm$^2$) | Lm (µm) | ISA (cm$^2$) |
| 1 Air / - | Sacrifice | 39.2±0,8 (8) | 1220±37 (8) | | |
| Air / - | Air / - | | | 38.6±0.9 (8) | 1248±37 (8) |
| 2 CS / - | Sacrifice | 43.4±1.2* (8) | 1058±31* (8) | | |
| CS / - | CS / - | | | 45.1±1.2‡ (8) | 1033±31‡ (8) |
| 3 CS / - | CS / uridine | | | 41.0±1.4† (8) | 1157±79† (8) |

Meaning of abbreviations: Lm= mean linear intercept; ISA= internal surface area of the lungs; CS= cigarette smoke exposure, air= exposure to room air; Number in brackets= number of animals used. * $p<0.05$ vs air exposure (4 months), ‡ $p<0.05$ vs air exposure (7 months), † $p<0.05$ vs CS (7 months)

Fig. 2

URIDINE AND URIDINE ANALOGUES FOR TREATMENT OF SPECIFIC LUNG DISEASES, NAMELY COPD AND PULMONARY FIBROSIS

PRIORITY

This application corresponds to the national phase of International Application No. PCT/EP2012/064481 filed Jul. 24, 2012 which, in turn, claims priority to European Patent Application No. 11.177357.8 filed Aug. 12, 2011, the contents of which are incorporated by reference herein in their entirety.

FIELD OF THE PRESENT INVENTION

The present invention relates to the new indications of chronic obstructive pulmonary disease (COPD) and idiophathic pulmonary fibrosis (IPF) for uridine and uridine analogues.

BACKGROUND OF THE PRESENT INVENTION

COPD is a major health problem and is the fourth most common cause of death in the developed countries. COPD represent a spectrum of obstructive airway diseases, including chronic bronchitis and pulmonary emphysema. Besides significant extrapulmonary effects that may contribute to the severity in individual patients, the pulmonary component of COPD is characterized by airflow limitation that is not fully reversible. The airflow limitation is usually progressive and associated with an abnormal inflammatory response of the lung to noxious particles or gases. Physiological abnormalities in COPD can e.g. include mucuous hypersection and ciliary dysfunction, hyperinflation and gas exchange abnormalities. The abnormal permanent enlargement of the airspaces distal to the terminal bronchioles accompanied by destruction of the alveolar wall and without obvious fibrosis is defined as pulmonary emphysema. Regarding the therapy of COPD, no drug has demonstrated effectiveness in halting the decline of lung function so far. Drug therapy is rather directed to maintain control of symptoms and prevent exacerbation and there is a need for new therapeutic alternatives.

Idiopathic pulmonary fibrosis (IPF) is a devastating pulmonary disease of unknown aetiology associated with a progressive deterioration in lung function and a fatal prognosis despite aggressive therapeutic attempts. IPF is characterized by aberrant proliferation of fibroblasts and deposition of extracellular matrix components leading to the progressive loss in lung function and respiratory failure. An imbalance between the synthesis and degradation of extracellular matrix molecules seems to be involved in the pathogenesis of IPF. At present there is no cure for IPF and the community is still in search of an optimal treatment for IPF.

Uridine nucleotides, the phosphate esters of uridine, had previously been proposed for the treatment of chronic obstructive pulmonary disease and cystic fibrosis, which is a hereditary form of fibrosis. Promotion of mucociliary clearance by uridine triphosphate (UTP) was suggested in WO 99/32085 in view of a treatment of cystic fibrosis. WO 99/09998 was directed to a method of hydrating lung mucus secretions by administering uridine diphosphate (UDP) or analogues thereof and treating e.g. cystic fibrosis and chronic obstructive pulmonary disease. UDP and UTP act on purinergic receptors belonging to the P2Y family. UDP is e.g. a potent agonist of the P2Y6 receptor and UTP activates the P2Y2 receptor. However, it had recently been suggested that purinergic signalling plays a role in pathogenesis of COPD and allergic airway inflammation. P2-receptor blockade prevented the development of emphysema in smoke-exposed mice by reducing the influx into the lungs of the inflammatory cells and P2Y2 receptor-deficient mice were shown to have reduced pulmonary inflammation after acute smoke exposure (Cicko S et al., Purinergic receptor inhibition prevents the development of smoke-induced lung injury and emphysema, J Immunol. 2010 Jul. 1; 185(1):688-97). Similarly, blocking of the P2Y6-receptor or P2Y6-receptor deficiency reduced cardinal features of experimental asthma (Paula Vieira R et al., P2Y6 Receptor Contributes to Airway Inflammation and Remodeling in Experimental Allergic Airway Inflammation, Am J Respir Crit Care Med. 2011 Apr. 21). An activation of these receptors might thus be counterproductive and there is still a need for compounds which can be applied for the treatment of chronic obstructive pulmonary disease and cystic fibrosis.

The nucleoside uridine, which does not carry any phosphate groups, was applied before in the treatment for reduction of mitochondrial toxicity caused by highly active antiretroviral therapy (HAART) in human and was described to be safe and efficacious (Walker U A and Venhoff N, Uridine in the prevention and treatment of NRTI-related mitochondrial toxicity, Antivir Ther. 2005; 10 Suppl 2:M117-23; EP 1365755 B1). Recently, it was also reported of uridine and its analogue 4-thiouridine in view of their protective role in acute lung inflammation. Uridine was described to suppress asthmatic airway inflammation based on an ovalbumin (OVA)-alum model and a model of house dust mite (HDM)-induced airway inflammation in mice (Müller T et al., Local administration of uridine suppresses the cardinal features of asthmatic airway inflammation, Clin Exp Allergy. 2010 October; 40(10):1552-60). 4-thiouridine was demonstrated to have anti-inflammatory effects similar to those of uridine (Evaldsson C et al., 4-thiouridine induces dose-dependent reduction of oedema, leucocyte influx and tumour necrosis factor in lung inflammation, Clin Exp Immunol. 2009 February; 155 (2):330-8). Experiments were conducted using a sephadex-induced acute lung inflammation model, which shows similarity in inflammatory profile to clinical asthma.

While the use of UDP and UTP had been suggested for the treatment of COPD and cystic fibrosis, but might actually be counterproductive, the role of uridine for the treatment or prevention of chronic obstructive pulmonary disease (COPD) or idiopathic pulmonary fibrosis (IPF) were unknown until now.

SUMMARY OF THE PRESENT INVENTION

It has now surprisingly been found that a compound of formula I is useful for the treatment or prevention of COPD or IPF.

The present invention is as defined in the claims. The compound of formula I is defined as:

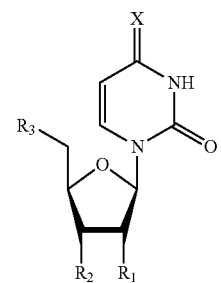

I wherein X represents O or S, $R_1$ represents H, OH or —O—($C_1$-$C_6$-alkanoyl) and $R_2$ and $R_3$ represent independently of each other OH or —O—($C_1$-$C_6$-alkanoyl).

In —O—($C_1$-$C_6$-alkanoyl) $C_1$-$C_6$-alkanoyl is bound by means of carbonyl to the oxygen. If one or several —O—($C_1$-$C_6$-alkanoyl) groups are present, —O—($C_1$-$C_4$-alkanoyl) is preferred, —O—($C_2$-$C_3$-alkanoyl) is more preferred and —O—($C_2$-alkanoyl) is most preferred. In —O—($C_1$-$C_6$-alkanoyl) $C_1$-$C_6$-alkanoyl can be straight chain or branched, where the number of carbon atoms allows for branched groups. Substituents $R_1$, $R_2$, and $R_3$ can be identical or different. In a particularly preferred embodiment of the present invention the substituents $R_1$, $R_2$, and $R_3$, are the same, most preferably OH or —O—($C_2$-alkanoyl). Especially preferred are compounds of the formula I wherein $R_1$, $R_2$, and $R_3$ each represent OH and X represents O (uridine), wherein $R_1$, $R_2$, and $R_3$ each represent OH and X represents S (4-thiouridine) and wherein $R_1$, $R_2$, and $R_3$ each represent —O—($C_2$-alkanoyl) and X represents O (triacetyluridine). The compound of formula I wherein $R_1$, $R_2$, and $R_3$ each represent OH and X represents O (uridine) is most preferred.

A compound of formula I is also referred to as the "active compound" or the "active compound of the invention" herein.

The active compound of the present invention is mainly applied for the treatment or prevention of COPD or IPF in human subjects, but it may also be employed in animals, such as e.g. dog.

BRIEF DESCRIPTION OF THE FIGURES

FIG. 2 is a representation of the morphometrical assessment of the effects of uridine on the progression of the emphysematous changes caused by cigarette smoke exposure.

DETAILED DESCRIPTION OF THE PREFERRED EMBODIMENTS

The effect of uridine and its analogues as a useful treatment or prophylactic measure of COPD can be seen e.g. from Examples 1 and 2. As cigarette smoke is a major risk factor for developing COPD, animal experiments were conducted to assess the effect of uridine treatment in mice with short or long-term smoke exposure.

Increasing evidences point to an important role of endogenous released ATP in the pathogenesis of COPD, as airway ATP-levels are correlating with disease severity (airflow limitation) and interference with the ATP/P2R-pathway has been shown to inhibit all cardinal features of COPD (Cicko S et al., Purinergic receptor inhibition prevents the development of smoke-induced lung injury and emphysema, J Immunol. 2010 Jul. 1; 185(1):688-97, Lucattelli M, Cicko S et al, P2X7 receptor signalling in the pathogenesis of smoke-induced lung inflammation and emphysema Am J Respir Cell Mol Biol. 2011 March; 44(3):423-9, Lommatzsch M et al., Extracellular adenosine triphosphate and chronic obstructive pulmonary disease, Am J Respir Crit Care Med. 2010 May 1; 181(9):928-34). Remarkably, the amount of extracellular ATP in BALF of smoke exposed mice treated with uridine could now significantly be reduced in a dose dependent manner compared to non uridine treated mice (FIG. 1b). Furthermore uridine treatment also dose dependently reduced the number of macrophages and neutrophils and the levels of pro-inflammatory cytokines IL-6 (interleukin-6), IFN-γ (interferon-gamma), IL-1-β (interleukin-1 beta), KC (keratinocyte derived chemokine), and MIP-2 (macrophage inflammatory protein-2), which are associated with the onset and/or maintenance of cigarette smoke induced lung inflammation in COPD.

In a murine model of chronic smoke exposure, which is characterized by the development of pulmonary emphysema, it was further shown that uridine treated mice showed a significantly lower mean linear intercept and a higher internal surface area of the lung as compared to non-uridine treated mice (FIG. 2). The determination of the average interalveolar distance (mean linear intercept) has become an accepted measure to confirm the presence of emphysema in various animal models. Exposure to smoke thus increased the mean linear intercept in the here applied murine model over control while treatment with uridine could reduce the deleterious effects of smoke.

The present invention is therefore directed to a compound of formula I for the prevention or preferably the treatment of COPD. According to the present invention, the treatment of COPD includes the treatment of the 4 stages of COPD (COPD GOLD I-IV) as defined by the Global Initiative for Chronic Obstructive Lung Disease (GOLD), and particularly also the treatment of emphysema. The active compound is further particularly suitable for the treatment of early stages of COPD as e.g. defined by COPD GOLD I-II.

Figure 3:
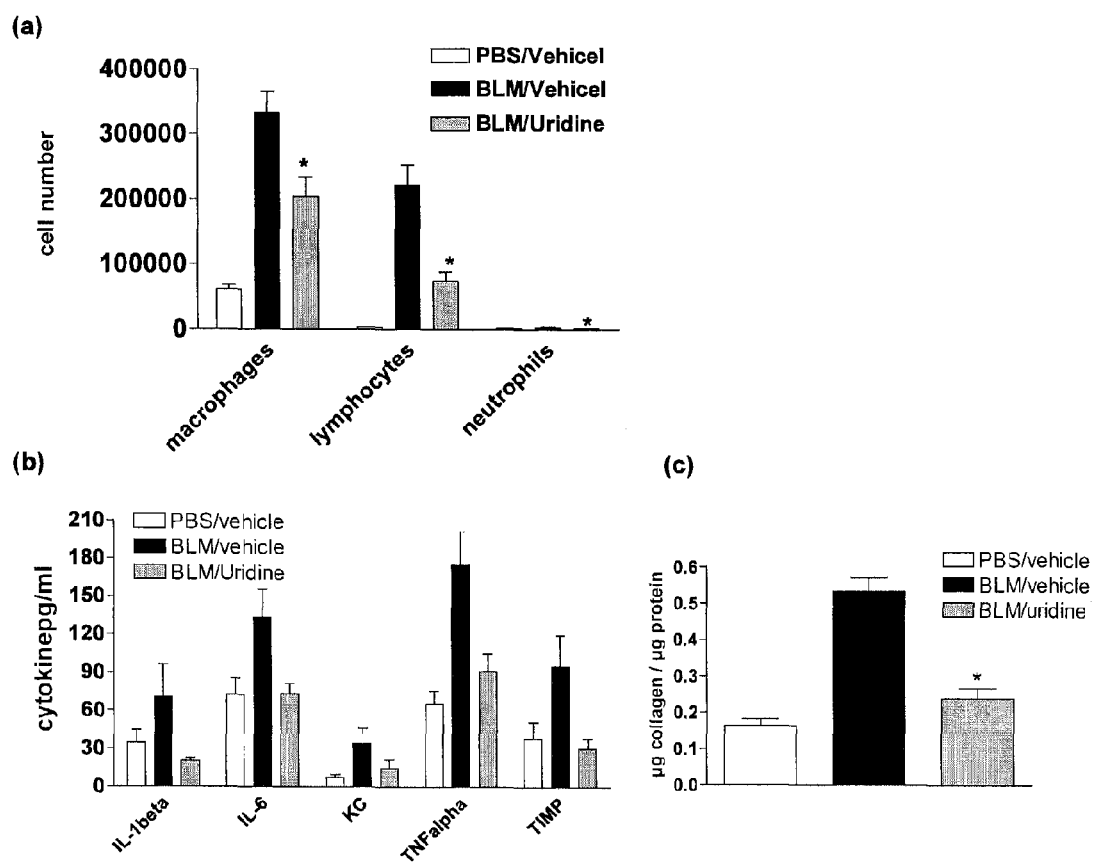
FIG. 3 demonstrates that uridine decreases BLM-induced pulmonary fibrosis. Lung fibrosis was induced by intrapulmonary application of BLM into C57/B16 male mice at day 0. Starting from day 14, animals were treated with either vehicle or uridine p.o 3x/week. At day 30 animals were killed and the differential-cell count (a), cytokine (b) in the BAL-fluid and the amount of collagen in lung (c) was analyzed. *$P<0.05$ BLM/vehicle treated vs. BLM/uridine treated animals.

Uridine treatment also turned out to be useful in the lung disease of IPF. Example 3 of the present invention demonstrated in a mouse model of bleomycin induced pulmonary fibrosis that treatment with uridine could significantly reduce the amount of collagen in the lung. Furthermore tissue inhibitor of metalloproteinases (TIMP-1), which plays a role in the extracellular control of matrix metalloproteinase (MMP) catalytic activity, was reduced to normal levels after bleomycin instillation when animals were treated with uridine in contrast to increased levels of TIMP-1 without uridine treatment (FIG. 3). Similarly, in the mouse model of bleomycin induced pulmonary fibrosis uridine treatment resulted in a down-regulation of proinflammatory cytokines, such as IL-1 beta (interleukin-1 beta), IL-6 (interleukin-6), KC (keratinocyte-derived chemokine) and TNFalpha (tumor necrosis factor-alpha) as well as a down-regulation of macrophages, lymphocytes and neutrophils in BALF.

The present invention thus also relates to a compound of formula I for the treatment of IPF and in particular against extracellular matrix accumulation.

From previously reported uridine supplementation in HIV lipoatrophy it is known that the active compound of the present invention is safe and well tolerable.

Any route of administration of the active compound of the invention to the subject of treatment can be employed. This includes e.g. an oral, nasal, inhalative or intravenous administration of the active compound whereby an oral or inhalative administration of the active compound of the invention are preferred.

The dosage of the active compound of the invention depends on different parameters, e.g. the substrate to which the active compound is administered, the substrate's body weight and age, the substrate's individual condition, the disease and severity of the disease and the route and frequency of administration. The active compound may e.g. be administered orally in a dose of 1-1000 mg/kg per day, preferably 5-500 mg/kg per day, which can be split up into several, e.g. 3, doses. For an inhalative administration the preferred dose of the active compound per inhalation is between 100 µg-1000 mg. Several of such doses can be administered successively and/or several times a day if needed.

The active compound of the invention is typically administered together with a pharmaceutical carrier.

The compound of the invention can be formulated into a pharmaceutical composition, which comprises an efficient amount of one or more active compounds of the invention. The active compound of the invention is typically contained in the pharmaceutical composition together or in a mixture with one or more organic and/or inorganic pharmaceutical carriers that can be fluid, solid or gaseous. Additionally, one or more other pharmaceutically active compounds for the treatment of COPD or IPF can be present.

For preparation of a solid pharmaceutical composition for oral administration the pharmaceutical carrier can specifically include e.g. fillers and binders such as cellulose derivates, microcrystalline cellulose, lactose, mannitol, xylitol, saccharose, starch, polyvinyl pyrrolidon and amylopectin. Disintegrating agents, lubricants and glidants can also be present. The pharmaceutical compositions may further be coated with an enteric coating. Solid pharmaceutical compositions for oral administration are preferably prepared in the form of tablets or capsules, e.g. hard or soft-gelatine capsules. Alternatively, a pharmaceutical composition for oral administration comprising the active compound may be prepared as powder to be packed in a container, e.g. a sachet. The content of the container can then be dissolved or suspended in e.g. water, juice or milk for an easy intake.

In preparation of an injectable pharmaceutical composition the active compound of the present invention is usually blended with pharmaceutical carriers and additives, such as e.g. pH-regulators, stabilizing agents, buffering agents and tonicity agents. It is also possible to prepare dry preparations to be reconstituted extemporaneously before injection.

For nasal administration the pharmaceutical composition can e.g. contain the active compound of the invention dissolved or suspended in a liquid pharmaceutical carrier, preferably being aqueous. Additives such as e.g. solubilising agents, surfactants and/or preservatives may be present.

For an inhalative administration the active compound of the invention can e.g. be delivered from a dry powder inhaler or as an aerosol spray from a pressurized container, with the active compound being suspended or dissolved in a liquefied suitable propellant, e.g. dichlorodifluoromethane, trichlorofluoromethane, dichlorotetra-fluoro-ethane, a hydrofluoroalkane such as 1,1,1,2-tetrafluoroethane or 1,1,1,2,3,3,3-heptafluoropropane, carbon dioxide or other suitable gas, or from a pump, spray or nebulizer that may contain a solution or suspension of the active compound. Where appropriate, the active compound can be formulated together with additives, e.g. solvents, buffers, amino acids, preservatives or surfactants. Capsules for use in an inhaler or cartridges may be formulated containing a powder mix which comprises the active compound. A dry powder for inhalation could e.g. be formulated by spray-drying the active compound with a sugar or sugar alcohol, such as lactose, trehalose or mannitol and other optional additives, e.g. buffers and amino acids.

The active compound of the invention can also be administered together with one or more other pharmaceutically active compounds for the treatment of COPD or IPF. Such other pharmaceutically active compounds for the treatment of COPD include e.g. short or long-acting $\beta_2$-agonists such as fenoterol, levalbuterol, salbutamol (albuterol), terbutalin or formoterol, arformoterol, indacaterol, salmeterol; short or long-acting anticholinergics such as ipratropium bromide, oxitropium bormide or tiotropium bromide; methylxanthines such as aminophylline and theophylline; glucocorticoids such as beclomethasone, budenoside, fluticason propionate, prednisone, methylprednisolone and phosphodiesterase-4 inhibitors such as roflumilast. For the treatment of IPF such other pharmaceutically active compounds include e.g. glucocorticoids such as prednisone or methylprednisolone; immunosuppressives or cytotoxic agents such as azathioprine and cyclophosphamide, cyclosporin A, methotrexate, chlorambucil, colchicine; and other agents that e.g. inhibit cytokines, proteases, oxidants or fibroblast growth factors; antioxidants; diphosphonates; inhibitors of leucocyte integrins.

The present invention thus also includes formulations which comprise the active compound of the invention and one or more other pharmaceutically active compound(s) in one and the same preparation, e.g. a tablet comprising both compounds. Equally included into the present invention are the concomitant or the timely staggered administration of the active compound and a pharmaceutically active compound in 2 different dosage forms, e.g. one tablet comprising the active compound of the invention and no other pharmaceutically active compound(s) for treatment of COPD or IPF and another tablet comprising one or more pharmaceutically active compound(s) for the treatment of COPD or IPF, but not the active compound of the present invention.

EXAMPLES

The examples hereafter are intended to illustrate the invention without however limiting it.

Example 1

Acute and Ongoing Cigarette Smoke Exposure

Male C57BL/6 mice were exposed to whole smoke of five cigarettes (commercial Virginia filter cigarettes: 12 mg of tar and 0.9 mg of nicotine) or room air for 20 min on three consecutive days in especially designed macrolon cages (Tecniplast, Buguggiate, Italy), as previously described (Cavarra E et al., Human SLPI inactivation after cigarette smoke exposure in a new in vivo model of pulmonary oxidative stress, Am J Physiol Lung Cell Mol Physiol. 2001 August; 281(2):L412-7, Cicko S et al., Purinergic receptor inhibition prevents the development of smoke-induced lung injury and emphysema, J Immunol. 2010 Jul. 1; 185(1):688-97). The smoke was produced by the burning of a cigarette and was introduced into the chamber with the airflow generated by a mechanical ventilator (7025 Rodent Ventilator, Ugo Basile, Biological Research Instruments, Comerio, Italy), at a rate of 250 ml/min. A second mechanical ventilator was used to provide room air for dilution (1:8) of the smoke-stream.

In some experiments, intratracheal treatment (i.t.) was performed prior to each smoke exposure: animals were anaesthetized by intraperitoneal injection of Ketamin/Xylazin and received an i.t. injection of uridine in a total volume of 80 µl (1 mM or 10 mM) or PBS which was used as vehicle. One hour after the last smoke challenge, mice were sacrificed and bronchoalveolar lavage (BAL) was performed.

To study the effect of Uridine in the ongoing cigarette smoke exposure mice were exposed to smoke on days 1-3 as described above. Then they were randomized to receive either vehicle (PBS) or Uridine peroral (p.o.) (200 µl 10 mM) 30 min before each of a series of three smoke or air challenges given at day 4-6 (as described above). At day 6 one hour after the last smoke/air challenge mice were killed and the bronchoalveolar lavage fluid (BALF) was collected.

Bronchoalveolar Lavage in Animals

BAL fluid was collected by cannulating the trachea under deep pentobarbital anesthesia and washing the lung three times with 1 ml PBS containing 0.1 mM EDTA, as previously described (Idzko M et al., Extracellular ATP triggers and maintains asthmatic airway inflammation by activating dendritic cells, Nat Med. 2007 August; 13(8):913-9, Cicko S et al., Purinergic receptor inhibition prevents the development of smoke-induced lung injury and emphysema, J Immunol. 2010 Jul. 1; 185(1):688-97). Total cell numbers were counted and differential cell counts were performed on cytospin preparations after staining with Diff-Quick (Medion Diagnostics, Dudingen, Switzerland). Differential cell counts were made on >200 cells using standard morphological criteria and FACS-analysis.

Flow Cytometry

After counting and washing, BAL cells were stained for 30 min with anti-MHC class II (macrophages/DC), anti-7/4 (Caltag) FITC (neutrophiles; Abd-Serotec, Dusseldorf, Germany), anti-CD3 and anti-CD19 cy-chrome (lymphocytes), and anti-CD 11c APC macrophages/DCs (eBioscience, San Diego, Calif.) in PBS containing 0.5% BSA and 0.01% sodium azide. Differential cell counts were analyzed by flow cytometry, as described previously (Idzko M et al., Extracellular ATP triggers and maintains asthmatic airway inflammation by activating dendritic cells, Nat Med. 2007 August; 13(8):913-9 and Cicko S et al., Purinergic receptor inhibition prevents the development of smoke-induced lung injury and emphysema, J Immunol. 2010 Jul. 1; 185(1):688-97).

ATP Measurements in BAL Fluid

To measure ATP concentrations in BALF in mice, fresh BALF supernatants were used, according to manufacturer's instructions (ATPlite Assay, PerkinElmer, Wellesley Mass.), but without the cell lysis step to avoid any contaminating intracellular ATP, as described previously (Idzko M et al., Extracellular ATP triggers and maintains asthmatic airway inflammation by activating dendritic cells, Nat Med. 2007 August; 13(8):913-9 Cicko S et al., Purinergic receptor inhibition prevents the development of smoke-induced lung injury and emphysema, J Immunol. 2010 Jul. 1; 185(1):688-97)).

Cytokine Measurement in BAL Fluid

Cytokine concentrations in BALF were measured using commercially available ELISA kits (R&D Systems, Minneapolis, Minn.) according to the manufacturer's recommendations.

Statistical Analysis

Statistical significance of differences between samples was calculated using ANOVA, followed by Bonferroni comparison test. Difference were considered significant if $p<0.05$.

Figure 1:
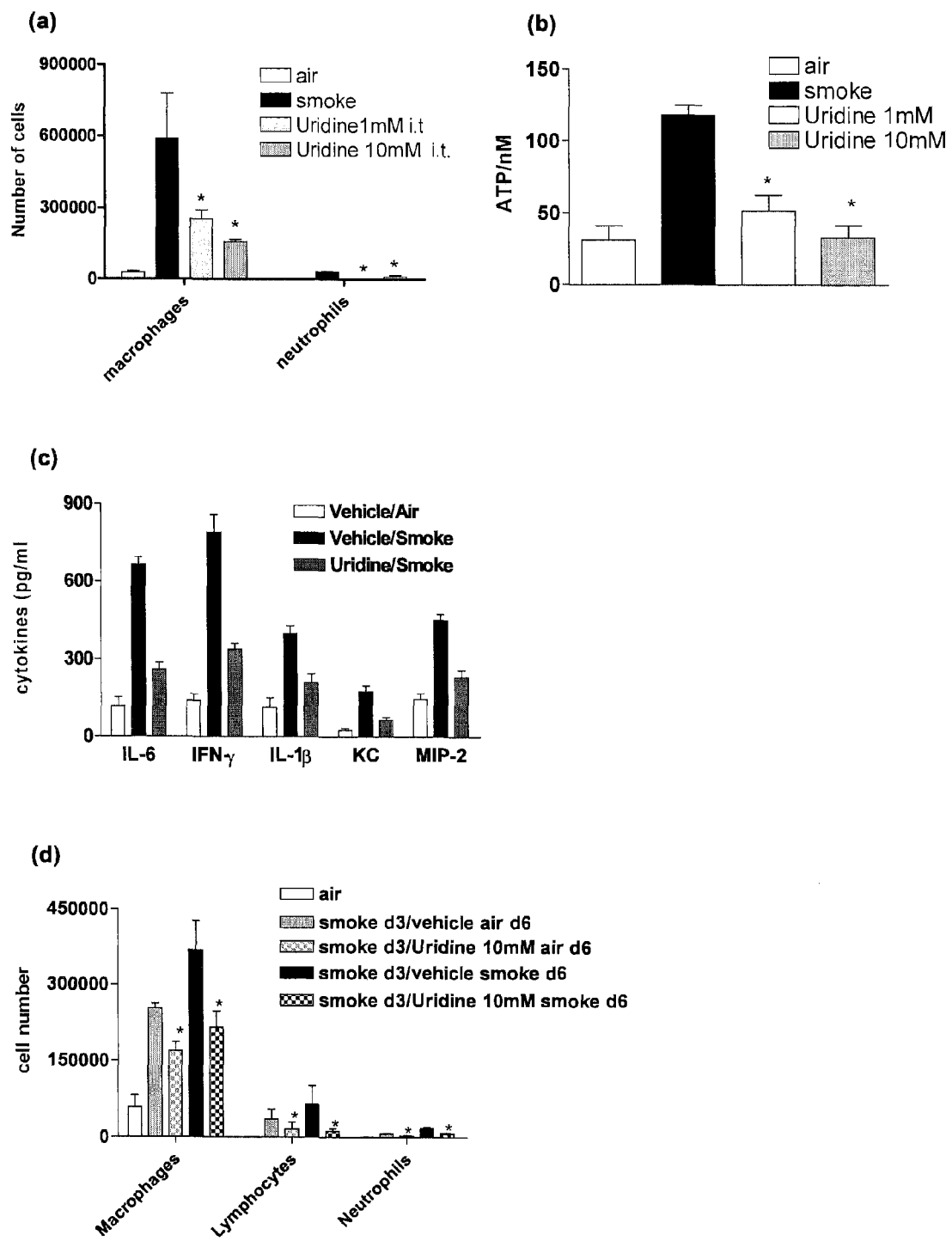
FIG. 1 depicts the effects of uridine on the response to acute and ongoing smoke exposure. Parts (a)-(c): Male C57BL/6 mice were left untreated or exposed to the smoke of 5 cigarettes on three consecutive days. Thirty minutes before smoke exposure animals received an i.t. injection of vehicle or different concentrations of Uridine. One hour after the last smoke exposure animals were killed and BAL fluid analyzed for (a) the number and distribution of cells, (b) for ATP-levels content and (c) levels of proinflammatory cytokine IL-6, IFNγ, IL-1β, KC and MIP-2. Data are shown as mean±SEM, n=5 mice in each group. *$P<0.05$, Uridine treated vs. vehicle treated smoke exposed animals. Part (d): Animals were left either untreated or exposed to the smoke of 5 cigarettes on three consecutive days, from day 4 smoke exposure was either continued or changed to ambient air. On day 4 to day 6 animals received a p.o. application of Uridine 200 μl 10 mM or Vehicle (PBS) 30 min prior to smoke or air exposure. On day 6 BALF differentials was analyzed. Data are shown as mean±SEM, n=5 mice in each group.*$P<0.05$ smoke/vehicle treated vs. smoke/uridine treated animals at the same time points.

Data of Example 1 are presented in FIG. 1.

Example 2

Chronic Exposure to Cigarette Smoke

The methodology for chronic smoke exposure has been previously described (Cavarra E et al., Human SLPI inactivation after cigarette smoke exposure in a new in vivo model of pulmonary oxidative stress, Am J Physiol Lung Cell Mol Physiol. 2001 August; 281(2):L412-7 Cicko S et al., Purinergic receptor inhibition prevents the development of smoke-induced lung injury and emphysema, J Immunol. 2010 Jul. 1; 185(1):688-97)). Briefly, male C57BL/6 mice were exposed to either the smoke of 3 cigarettes per day (commercial Virginia filter cigarettes: 12 mg of tar and 0.9 mg of nicotine), 5 days per week or to room air (controls) for 4 or 7 months, respectively. When indicated, animals received an oral treatment by gavage with Uridine (0.6 mg/kg) 45 min prior to smoke exposure.

Histology

At the end of the respective time period, animals were sacrificed; BAL was performed followed by lung resection. The lungs were fixed intratracheally with formalin (5%) at a pressure of 20 cm $H_2O$. Lung volume was measured by water displacement. All lungs were then dehydrated, cleared in toluene, and embedded under vacuum in paraffin. Two 7 µm transversal sections were made and stained with hematoxylin-eosin. Two pathologists blinded to the exposure protocol carried out morphological and morphometrical evaluation. Morphometrical assessment included determination of the average interalveolar distance (mean linear intercept: Lm) (Cicko S et al., Purinergic receptor inhibition prevents the development of smoke-induced lung injury and emphysema, J Immunol. 2010 Jul. 1; 185(1):688-97) which represents the average size of air space (alveolar ducts, alveolar sacs, and alveoli), and of the internal surface area of the lungs (ISA). Lm is the length of a test line placed over histologic slides of the lung, divided by the number of times the line crosses alveolar walls (not surfaces). Fields with bronchi, large bronchioli, or blood vessels were excluded from the measurements. Following formula was used for the calculation of the Lm: Lm=the total length of 50 lines/the number of alveoli intercepts.

This Lm value was used to calculate the ISA (which represent the gas exchange surface), necessary for evaluating the degree of emphysema, from the equation 4V/Lm, where V is the postfixation lung volume. For the determination of the Lm for each pair of lungs, 40 histological fields were evaluated both vertically and horizontally.

Examination of these numbers of fields meant that practically the entire lung area was evaluated.

Statistical Analysis

Statistical significance of differences between samples was calculated using ANOVA, followed by Bonferroni comparison test. Difference were considered significant if $p<0.05$.

Data of Example 2 are presented in FIG. 2.

Example 3

Mouse Model of Bleomycin (BLM) Induced Pulmonary Fibrosis

The induction of BLM induced pulmonary fibrosis was performed as previously described (Gasse P, Mary C, Guenon I, Noulin N, Charron S, Schnyder-Candrian S, Schnyder B, Akira S, Quesniaux V F, Lagente V, et al. Il-1r1/myd88 signaling and the inflammasome are essential in pulmonary inflammation and fibrosis in mice. J Clin Invest 2007; 117 (12):3786-3799). Then, male C57/Bl6 animals were treated with the uridine p.o. (200 µl 10 mM) or vehicle 14 days after BLM-instillation for 3 days a week. At day 30 animals were examined for the typical features of BLM-induced lung injury. Therefore BALF was collected and differential cell count was analyzed as described above.

Cytokine Measurement in BAL Fluid

Cytokine concentrations in BALF were measured using commercially available ELISA kits (R&D Systems, Minneapolis, Minn.) according to the manufacturer's recommendations.

Amount of Collagen in Lung

The amount of lung collagen was measured in the lung tissue using the Sircol-assay according to the manufacturer's recommendations (Biocolor, Life-Science, UK).

Statistical Analysis

Statistical significance of differences between samples was calculated using ANOVA, followed by Bonferroni comparison test. Difference were considered significant if p<0.05.

Data of Example 3 are presented in FIG. 3.

The invention claimed is:

1. A method of treating or preventing chronic obstructive pulmonary disease or idiopathic pulmonary fibrosis in a subject in need thereof, said method comprising the step of administering by inhalation the pharmaceutical formulation comprising uridine in a dose that comprises between 100 µg and 1000 mg of compound per inhalation to said subject.

2. The method according to claim 1, wherein the formulation further comprising one or more other pharmaceutically active compounds suitable for the treatment of COPD or IPF selected from the group consisting of: short-acting β2-agonists, long-acting β2-agonists, short-acting anticholinergies, long-acting anticholinergies, methylxanthines, glucocorticoids, phosphodiesterase-4inhibitors, immunosuppressive agents, cytotoxic agents, agents that inhibit cytokines, agents that inhibit proteases, agents that inhibit oxidants, agents that inhibit fibroblast growth factors, antioxidants, diphosphonates, and inhibitors of leucocyte integrins.

3. The method according to claim 1, wherein the formulation further comprises a propellant.

4. The method according claim 1, wherein the formulation further comprises or more other pharmaceutically active compounds suitable for the treatment of COPD selected from the group consisting of: fenoterol, levalbuterol, salbutamol (albuterol), terbutalin, formoterol, arformoterol, indacaterol, salmeterol, ipratropium bromide, oxitropium bormide, tiotropium bromideaminophylline, theophylline, beclomethasone, budenoside, fluticason propionate, prednisone, methylprednisolone, and roflumilast.

5. The method according claim 1, wherein the formulation further comprises or more other pharmaceutically active compounds suitable for the treatment of IPF selected from the group consisting of: prednisone, methylprednisolone, azathioprine, cyclophosphamide, cyclosporin A, methotrexate, chlorambucil, and colchicine.

* * * * *